United States Patent
Babaev

(10) Patent No.: US 6,723,064 B2
(45) Date of Patent: *Apr. 20, 2004

(54) ULTRASONIC CATHETER DRUG DELIVERY METHOD AND DEVICE

(75) Inventor: Eilaz Babaev, Minnetonka, MN (US)

(73) Assignee: Advanced Medical Applications, Inc., Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/454,654

(22) Filed: Jun. 4, 2003

(65) Prior Publication Data

US 2003/0229304 A1 Dec. 11, 2003

Related U.S. Application Data

(63) Continuation of application No. 09/813,577, filed on Mar. 21, 2001, now Pat. No. 6,623,444.

(51) Int. Cl.[7] .............................................. A61B 17/20
(52) U.S. Cl. ........................................ 604/22; 606/169
(58) Field of Search ............................. 604/21, 22, 27, 604/13; 606/169

(56) References Cited

U.S. PATENT DOCUMENTS

| | | | | | |
|---|---|---|---|---|---|
| 4,750,488 | A | * | 6/1988 | Wuchinich et al. | 606/128 |
| 5,474,530 | A | * | 12/1995 | Passafaro et al. | 604/22 |
| 5,605,537 | A | * | 2/1997 | Ivey | 604/21 |
| 5,735,811 | A | * | 4/1998 | Brisken | 604/22 |
| 6,007,513 | A | * | 12/1999 | Anis et al. | 604/22 |

* cited by examiner

Primary Examiner—Edward K. Look
Assistant Examiner—John K Fristoe, Jr.
(74) Attorney, Agent, or Firm—Carter, DeLuca, Farrell & Schmidt, LLP

(57) ABSTRACT

An ultrasonic catheter drug delivery device comprises an ultrasound transducer to produce ultrasonic waves, which transducer is mechanically attached to a catheter body or chamber. The ultrasonic transducer has a distal tip with a distal radiation surface, and when a therapeutic agent from a fluid source is directed to the catheter body or chamber, the radiation surface creates ultrasonic pressure and delivers liquid and simultaneously ultrasonic energy to a patient's vascularity or a selected body lumen. The method applies therapeutic agent and ultrasonic waves to the vascular area, lung or any body lumen without requiring direct contact between ultrasound transducer and body, dissolves blood clots, and stimulates tissue cells.

22 Claims, 3 Drawing Sheets

ULTRASONIC CATHETER DRUG DELIVERY METHOD AND DEVICE

This application is a continuation of application Ser. No. 09/813,577 filed Mar. 21, 2001 now U.S. Pat. No. 6,623,444.

FIELD OF THE INVENTION

The present invention generally relates to medical devices and methods. More particularly, the present invention relates to apparatus and methods for the ultrasonically enhanced delivery of therapeutic or contrast agents within the vascular and lung areas or other corporeal lumens.

BACKGROUND OF THE INVENTION

Despite the significant progress of medical technology, vascular and lung diseases, as well as arterial thrombosis (blood clots in arteries), remain frequent, costly and serious problems in health care. Current methods of treatment such as drugs, interventional devices, and/or bypass surgery are usually expensive and not always effective, even sometimes causing additional problems. For example, drugs can also dissolve beneficial clots or interventional devices can injure healthy tissue to cause potentially fatal bleeding complications or to form scarring or cellular growth which may itself eventually become a serious obstruction in, for example, a blood vessel (a process known as restenosis).

Ultrasonic energy has been used for enhancing the intravascular delivery of drug, to dissolve clot acoustically, disrupt mechanically and inhibit restenosis. Such energy can be delivered intravascularly using specialized catheters having ultrasonically vibrating surface at or near their distal ends. One type of ultrasonic catheter delivery system uses a wire or other axial transmission element to deliver energy from an ultrasonic energy source, located outside the patient to the internal organs, to desired corporeal lumens. (See, for example, U.S. Pat. Nos. 5,002,059, 5,324,255, 5,345,940, and 5,699,805, each of which is incorporated herein by reference.) Such catheters are rigid and cannot be easily inserted through narrow and tortuous vessels and may cause serious damage to vascular walls.

A second type of catheter has ultrasonic transducers mounted directly on their distal ends. See, for example; U.S. Pat. Nos. 5,362,309, 5,318,014, 5,315,998, 5,269,291, 5,197,946, 6,001,069, and 6,024,718, each of which is incorporated herein by reference. Despite enhanced safety and the fact that there is no need to employ a transmission element along the entire length, these catheters suffer from limited ultrasound energy, and the transducer-catheter design is still problematic.

Another type of catheter has an ultrasonic transducer or ultrasound transmission element with a central orifice in the distal end to impart ultrasonic energy into liquid and simultaneously deliver it to a corporeal lumen. See, for example, U.S. Pat. Nos. 5,735,811 and 5,197,946, each of which is incorporated herein by reference. Although these catheters are more effective and liquid delivery is more convenient, there are design difficulties and limitation of ultrasound energy from longitudinal waves.

OBJECT OF THE INVENTION

It is an object of the invention to provide an improved method and device for catheter drug delivery.

It is also an object of this invention to provide a method and device for catheter drug delivery using ultrasound energy.

It is another object of the invention to mix different drugs ultrasonically and deliver them to a desired corporeal lumen ultrasonically.

It is a yet another object of the invention to mix drug-liquid solutions with a gas (for example, saline with oxygen) ultrasonically and deliver the mixture to a desired corporeal lumen ultrasonically.

It is a further object of the invention to provide a method and device for delivering drugs to an intravascular area or/and a corporeal lumen, to dissolve blood clots.

It is a yet further object of the invention to treat a blocked and narrowed blood vessel with ultrasound waves.

These and other objects of the invention will become more apparent from the discussion below.

SUMMARY OF THE INVENTION

The present invention relates to apparatus and method for the ultrasonically enhanced delivery of therapeutic or contrast agents within the vascular and lung area or other desired corporeal lumens. Ultrasonic waves are applied to a vascular area, lung or any corporeal lumen without requiring direct contact between ultrasound transducer tip and the patient's body, particularly to dissolve blood clots.

According to the present invention, a catheter system comprises an ultrasound transducer having a distal tip with a radial surface and a distal end surface. The ultrasound transducer is disposed in a chamber at the proximal end of the catheter, and the transducer radiation surface or tip directs ultrasound waves or energy forward into the catheter coaxially via liquid. Longitudinal ultrasound waves induce wave motion in fluid adjacent to the transducer distal end. While particularly intended to enhance the absorption of therapeutic agents delivered to certain body lumens, the catheter system of the present invention is also useful for the delivery of ultrasonic energy to a desired location. The transducer radiation surface or transducer tip, may be cylindrical, flat, concave, convex, irregular or have a different shape-geometry to radiate ultrasound energy into catheter.

The catheter of the present invention may comprise a proximal tubing for delivering therapeutic agent from a reservoir by pump or syringe. The tubing may be located in front of or behind the radiation surface.

In a first embodiment of the invention, an ultrasound transducer and tip are mounted in a proximal portion of a catheter body, located outside of the body of a patient. The remainder of the catheter distal to the proximal portion may be inserted into a blood vessel or attached to a body lumen, to drive a therapeutic agent ultrasonically and/or deliver ultrasonic energy.

In a second embodiment, the distal tip of the transducer does not have an orifice, which is very important to create and deliver ultrasound energy fully to a vessel or body lumen.

In a third embodiment, the catheter system comprises a catheter body, mechanically coupled with an ultrasound transducer through a housing or tip node, which is where the transducer body is outside the catheter. In this way, the catheter body can be provided with two or more tubing inlets (sleeves) for different therapeutic agents, even one or more different gases such as oxygen, and agents to be mixed and delivered ultrasonically.

The catheter system of the invention is particularly advantageous on tissues for which local topical application of a therapeutic agent is desirable but contact with the tissue is to be avoided. Furthermore, ultrasound waves used in the method energize the drug, dissolve the clots and cause the penetration of the drug within the narrow and blocked vessels.

DETAILED DESCRIPTION OF THE INVENTION

The present invention is a method and device, which provides treatment of luminal conditions, particularly for the treatment of coronary and peripheral arterial disease and thrombosis, where the purpose is to dissolve or disrupt the clot, plague or other stenotic lesions which cause the disease, and for dilation of narrowed vessels. The method and device of the present invention also useful to enhance the administration of therapeutic agents primarily responsible for the disruption of the clots or other stenotic material. The ultrasonic energy agitates and promotes the penetration of the drug into the stenotic material. Due to delivery of therapeutic agent and ultrasound energy through the agent, this method and device of the present invention are further useful for treatment of other body lumens, such as the urethra, ureter, fallopian tubes, or urological disorders related with prostate gland (BPH—Benigh Proctatic Hyperplasia), and can be used for impotency (erectile dysfunction) treatment by ultrasonically stimulating sexual organs, urinary tract, and the like.

The present invention can be used for targeted and localized drug delivery for treatment of lung, vasculature, vasopasm and tumor treatment. In addition, this invention is very useful for the treatment of closed wounds as a fistulas, canals, etc., by destroying bacteria cells and stimulating healthy tissue cells.

Figure 1:
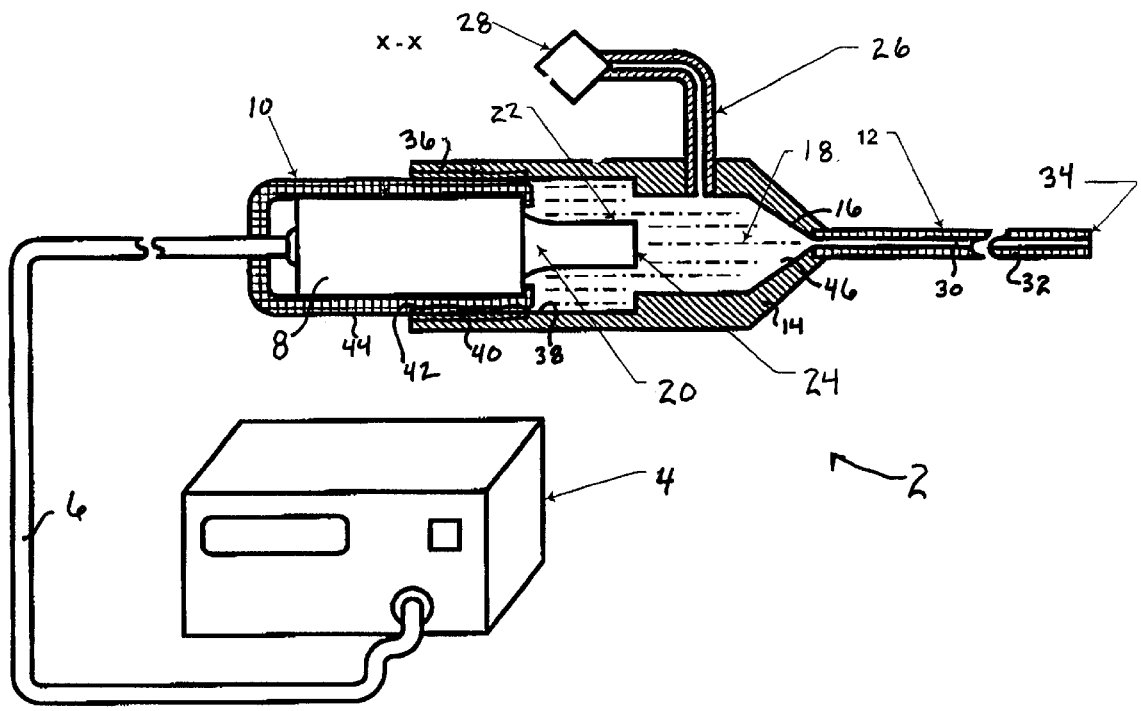
FIG. 1 is a perspective, partly cross-sectional view of an ultrasonic catheter drug delivery system for use according to the present invention.

The invention can perhaps be better appreciated by referring to the drawings. FIG. 1 is a perspective view of ultrasound catheter drug delivery system 2, comprising an ultrasound generator 4, a connector 6 operatively connecting ultrasound generator 4 with a transducer 8, a housing 10 surrounding transducer 8, and a catheter 12 having a proximal portion 14 with a chamber 16 containing a therapeutic agent 18. Transducer 8 has a tip 20 with a radial surface 22 and a distal radiation surface 24. Chamber 16 is in fluid communication through tubing 26 with a fluid source 28, and directly with at least one lumen 30 of the distal portion 32 of catheter 12 that extends to catheter distal end 34. Fluid source 28 can be, for example, a reservoir with a pressure pump or syringe.

The proximal section 36 of catheter proximal portion 14 sealingly engages housing 10. Preferably the inner surface 38 of proximal section 36 has threads 40 that engage reciprocal threads 42 on the outer surface 44 of housing 10. This arrangement will allow the operator to vary the distance between distal radiation surface 24 and the distal end 46 of chamber 16 to regulate ultrasonic pressure and energy level. While radial surface 22 can be smooth or substantially smooth, it is preferred that this surface is not smooth, for example, with rings, threads, barbs, or the like, which will create more ultrasonic pressure in catheter 12.

In the embodiment of the invention shown in FIG. 1, ultrasonic energy at a preselected frequency is sent through the catheter 10 with fluid such as a therapeutic agent as a transmission member. Ultrasound energy will pass through therapeutic agent 18 to catheter distal end 34. Catheter 12 may be formed from a conventional rigid or flexible material, dependent upon the application. It would be appropriate for catheter 12 to be flexible if the catheter is to be inserted into tortuous vascularity or if catheter distal end 34 is to be attached to a vessel, fistula, or the like.

Figure 2:
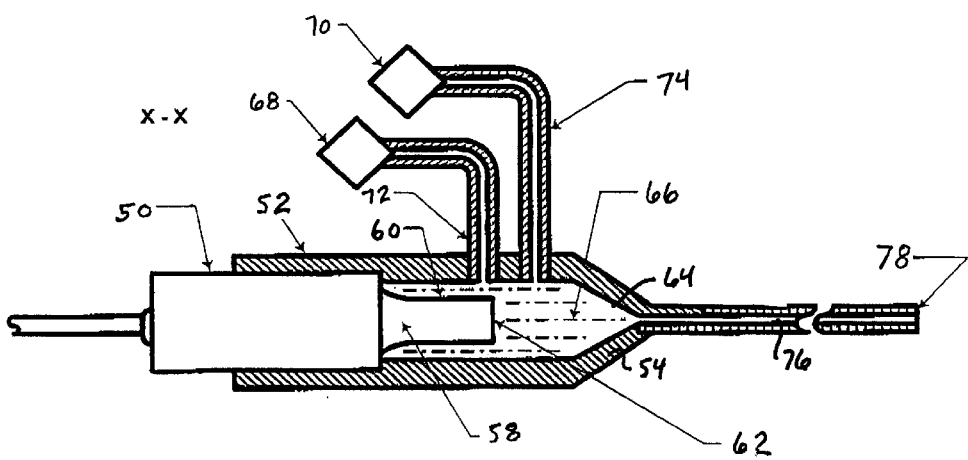
FIG. 2 is a lateral view of an ultrasonic catheter system chamber of the invention with two horizontally located sleeves.

A second embodiment of the invention is shown in FIG. 2, where transducer 50 is fixedly, optionally removably, attached to the proximal section 52 of the proximal portion 54 of a catheter 56. Transducer 50 has a tip 58 with a radial surface 60 and a distal radiation surface 62. Catheter proximal portion 54 has a chamber 64 with a therapeutic agent 66 that is in fluid communication with each of two fluid sources 68,70 through lumens 72,74, respectively. Fluid sources 68,70 may provide two or more fluids, e.g., liquid or gas, such as saline or oxygen, to be ultrasonically mixed and delivered through lumen 76 to catheter distal end 78.

Figure 3:
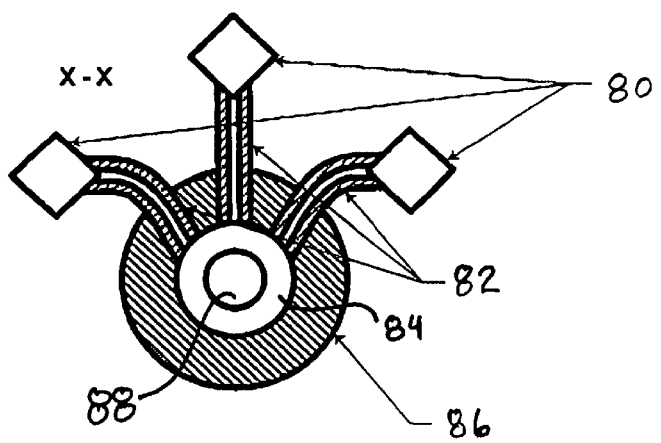
FIG. 3 is a frontal view of an ultrasonic catheter system chamber of the invention with three peripherally located sleeves.

FIG. 3 is a semi-cross-sectional view of the proximal end of a catheter according to the invention wherein three fluid sources 80 are each in fluid communication through a lumen 82 with chamber 84 of catheter proximal section 86. The distal radiation surface 88 of a transducer (not shown) is positioned within chamber 84.

Figure 4:
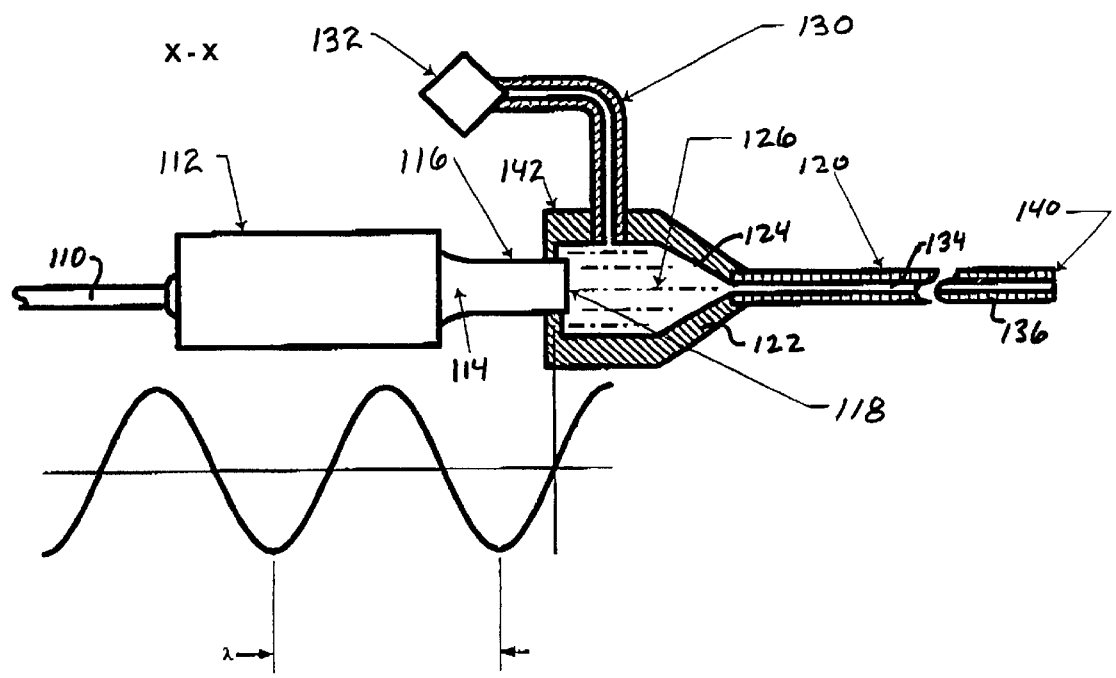
FIG. 4 is a lateral, cross-sectional view of a catheter system chamber, mechanically coupled with an ultrasound transducer through the tip.

In FIG. 4, a connector 110 operatively connects an ultrasound generator (not shown) with a transducer 112, which has a tip 114 with a radial surface 116 and a distal end surface 118. A catheter 120 has a proximal portion 122 with a chamber 124 containing a therapeutic agent 126. Chamber 124 is in fluid communication through tubing 130 with a fluid source 132, and directly with at least one lumen 134 of the distal portion 136 of catheter 120 that extends to catheter distal end 140. Fluid source 132 can be, for example, a reservoir with a pressure pump or syringe.

The proximal section 142 of catheter proximal portion 122 sealingly engages radial surface 116. Chamber 124 must be attached to ultrasonic transducer distal tip 114 at the mechanical resonant node, such as node 144. If chamber 124 is not connected to the resonant node (either a little before or a little after the mechanical node), the intensity of the ultrasound energy at distal end 140 will be attenuated, i.e., damped, and ultrasound waves and/or energy will be transferred to the walls of chamber 126, possibly damaging the chamber 126 structure assembly, which may cause leakage.

Figure 5:
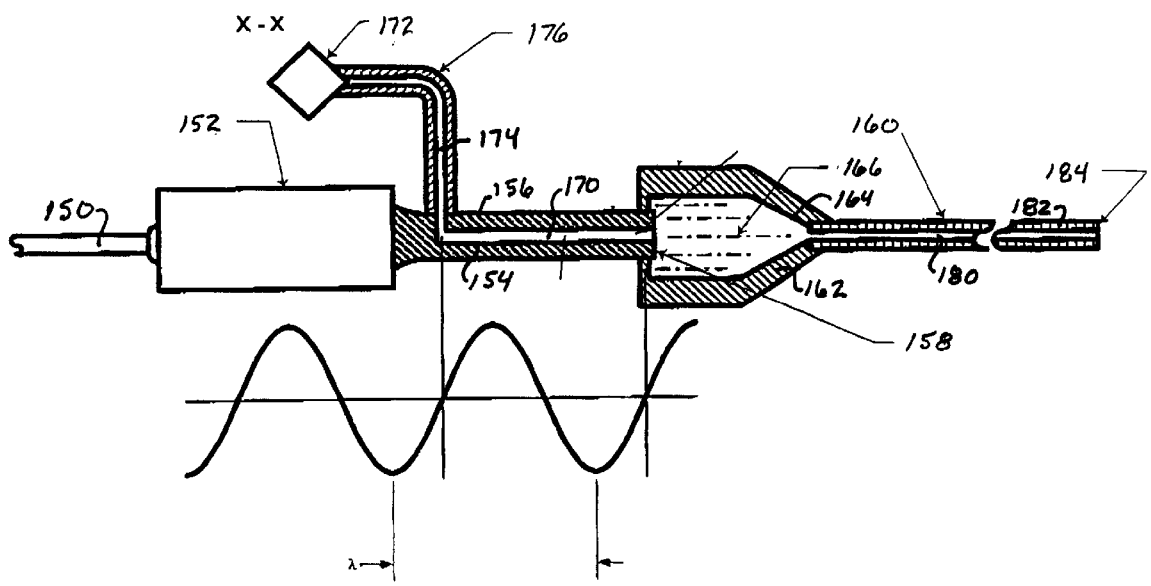
FIG. 5 is a lateral, cross-sectional view of an ultrasonic catheter drug delivery system for delivering therapeutic agent to the catheter body or chamber through a central orifice of the ultrasonic tip.

In the embodiment of the invention set forth in FIG. 5, a connector 150 operatively connects an ultrasound generator (not shown) with a transducer 152, which has a distal tip 154 with a radial surface 156 and a distal end surface 158. A catheter 160 has a proximal portion 162 with a chamber 164 containing a therapeutic agent 166.

Transducer distal tip 154 has a central orifice 170. Chamber 164 is in fluid communication with at least one fluid source 172 through central orifice 170, which can be smooth, waved, ringed, slotted, grooved, or threaded, and infusion lumen 174 within tubing 176. Two or more fluid sources 172 and infusion lumens 174 can mix and deliver different therapeutic agents. Chamber 164 is also in fluid communication with lumen 180 in the distal portion 182 of catheter 160 that extends to distal end 184. The non-smooth surface of orifice 170, such as rings or threads, increases the pressure of liquid in chamber 164.

Chamber 164 should be attached to ultrasonic transducer distal tip 158 at a mechanical resonant node, such as node 190. Similarly, each lumen 174 should intersect central orifice 170 at a resonant node, such as node 192.

The catheter systems herein are comprised of conventional materials. The transducer and catheter chamber are preferably comprised of suitable metallic or even polymeric substances. Most preferably the transducer distal tip is comprised of a metal such as titanium or nitinol.

As is mentioned throughout, the invention here can deliver one or more liquid or gaseous substances to a catheter distal end. Such substances include, but are not limited to, therapeutic agents such as antibiotics or antiseptics, saline, oil, water, oxygen, anticoagulants such as heparin or cumadine, or even liquid medical polymers, or mixtures of two or more thereof.

The preceding specific embodiments are illustrative of the practice of the invention. It is to be understood, however, that other expedients known to those skilled in the art or disclosed herein, may be employed without departing from the spirit of the invention or the scope of the appended claims.

What is claimed is:

1. A catheter system for ultrasound drug delivery, comprising:
   a catheter having a proximal portion comprising a chamber and a distal end, wherein at least one lumen extends longitudinally from said chamber to said distal end;
   at least one fluid source in fluid communication with said chamber and providing at least one fluid; and
   an ultrasound transducer having a distal end configured and dimensioned to propagate ultrasound waves through said catheter, wherein said ultrasound waves are propagated by the at least one fluid within at least a portion of said catheter by inducing wave motion in said at least one fluid to deliver fluid and/or ultrasound energy to the catheter distal end.

2. The catheter system of claim 1, wherein the transducer distal tip is positioned coaxially outside the chamber.

3. The catheter system of claim 1, wherein wave motion is induced in the at least one fluid adjacent to the transducer distal end.

4. The catheter system of claim 1, wherein the at least one fluid and ultrasound energy are delivered simultaneously to the catheter distal end.

5. The catheter system of claim 1, wherein the transducer distal tip has a central orifice in fluid communication with a fluid source of said at least one fluid source and said chamber.

6. The catheter system of claim 5, wherein the surface of the orifice is non-smooth.

7. The catheter system of claim 5, wherein the orifice surface is ringed, slotted, waved, grooved, or threaded.

8. The catheter system of claim 5, wherein the orifice is configured and dimensioned for admixing the at least one fluid from the at least one fluid source therein.

9. The catheter system of claim 1, wherein the transducer is capable of operating at a frequency of from about 10 kHz to $10^3$ MHz.

10. The catheter system of claim 1, wherein the transducer distal tip comprises a radial surface and a distal radiation surface.

11. The catheter system of claim 10, wherein the radial surface is not smooth.

12. The catheter system of claim 10, wherein the radial surface is ringed, slotted, waved, grooved, or threaded.

13. The catheter system of claim 10, wherein the distal radiation surface is flat, conical, oval, circular, semi-spherical, square, or rectangular.

14. The catheter system of claim 1, wherein the at least one fluid is a therapeutic agent.

15. The catheter system of claim 1, wherein at least a portion of the ultrasound transducer can be moved backward and/or forward to change ultrasound pressure and/or delivered ultrasound energy level.

16. A catheter system for ultrasonically treating an interior area of the body, the system comprising:
    a catheter having at least one lumen;
    a transducer having a distal radiation surface configured and dimensioned for coupling with a proximal end of the catheter and for emitting ultrasonic energy therein; and
    at least one fluid source for introducing at least one fluid within the proximal end of the catheter, wherein the emitted ultrasonic energy is delivered to the interior area of the body by the at least one fluid through the at least one lumen for treating the interior area of the body with ultrasonic energy.

17. The catheter system according to claim 16, wherein the transducer operates at a frequency from 10 kHz to 10,000 MHz.

18. The catheter system according to claim 16, further comprising means for translating the distal radiation surface for regulating at least one characteristic of the emitted ultrasonic energy.

19. The catheter system according to claim 16, further comprising means for sealingly engaging the distal radiation surface within the proximal end of the catheter.

20. An internal treatment method comprising the steps of:
    inserting at least a portion of an ultrasound emitting catheter into a body to be treated, wherein said ultrasound catheter includes an ultrasound transducer with a distal radiation end in fluid communication with the catheter distal tip through at least one lumen, said at ultrasound catheter further including a chamber for introducing at least one fluid therein from at least one fluid source;
    guiding the catheter to an internal treatment site;
    introducing the at least one fluid within said chamber; and
    actuating the ultrasound transducer to emit ultrasonic energy for being propagated via the at least one lumen to the treatment site by said at least one fluid.

21. A treatment method as in claim 20, wherein the ultrasonic catheter has a user-adjustable ultrasonic frequency range including at least a plurality of frequencies between 10 kHz and 1000 MHz.

22. A treatment method as in claim 20, wherein said treatment is beneficial for the promotion of healthy tissue growth or treatment of conditions in the group consisting of ailments affecting urethra, ureter, and fallopian tubes, impotency, and urological disorders related with prostate gland.

* * * * *